US008944129B2

(12) United States Patent
Yamamoto

(10) Patent No.: US 8,944,129 B2
(45) Date of Patent: Feb. 3, 2015

(54) APPARATUS FOR MANUFACTURING A DISPOSABLE WEARING ARTICLE

(75) Inventor: Hiroki Yamamoto, Kagawa (JP)

(73) Assignee: Unicharm Corporation, Ehime-ken (JP)

(*) Notice: Subject to any disclaimer, the term of this patent is extended or adjusted under 35 U.S.C. 154(b) by 179 days.

(21) Appl. No.: 13/500,007

(22) PCT Filed: Oct. 7, 2010

(86) PCT No.: PCT/JP2010/067658
§ 371 (c)(1),
(2), (4) Date: Jun. 14, 2012

(87) PCT Pub. No.: WO2011/043423
PCT Pub. Date: Apr. 14, 2011

(65) Prior Publication Data
US 2012/0247681 A1   Oct. 4, 2012

(30) Foreign Application Priority Data

Oct. 7, 2009   (JP) ................................ 2009-233837

(51) Int. Cl.
*B32B 38/18* (2006.01)
*B32B 38/04* (2006.01)
*A61F 13/15* (2006.01)

(52) U.S. Cl.
CPC ..... *A61F 13/15609* (2013.01); *A61F 13/15764* (2013.01); *A61F 13/15804* (2013.01)
USPC ........... 156/511; 156/440; 156/494; 156/549; 156/574

(58) Field of Classification Search
CPC . A61F 2013/1591; B32B 38/18; B32B 38/04; B65H 54/00; B65H 57/006
USPC ......... 156/440, 494, 511, 549, 574, 161, 229, 156/179, 178, 177, 176, 167, 166, 263, 256
See application file for complete search history.

(56) References Cited

U.S. PATENT DOCUMENTS 5,221,390 A * 6/1993 Persson et al. ................ 156/164
5,342,341 A   8/1994 Igaue et al.
(Continued)

FOREIGN PATENT DOCUMENTS

JP   4317650   11/1992
JP   2849234   11/1998
(Continued)

OTHER PUBLICATIONS

Office Action issued Feb. 7, 2014, corresponds to Eurasian patent application No. 201200386/31.
(Continued)

*Primary Examiner* — Linda L Gray
(74) *Attorney, Agent, or Firm* — Lowe Hauptman & Ham LLP

(57) ABSTRACT

A diaper manufacturing apparatus according to the present invention includes: an oscillating mechanism disposed on a top-sheet continuous body while oscillating leg gathers; an outer holding mechanism holding the leg gathers disposed in a predetermined waveform by the oscillating mechanism; and a cutting mechanism having a blade section cutting the leg gathers held by the outer holding mechanism. The outer holding mechanism holds, out of a region formed in a predetermined waveform, an outer end region OT which includes an outer end of the leg gathers and on which an adhesive is not applied. The blade section is disposed inside, relative to a crossing direction, the outer end region OT held by the outer holding mechanism.

10 Claims, 13 Drawing Sheets

(56) References Cited

U.S. PATENT DOCUMENTS

| | | | |
|---|---|---|---|
| 5,413,654 A | 5/1995 | Igaue et al. | |
| 6,287,409 B1 | 9/2001 | Stephany | |
| 6,905,565 B2 | 6/2005 | Shimoe | |
| 2001/0025165 A1 | 9/2001 | Shimoe | |
| 2005/0000628 A1* | 1/2005 | Norrby | 156/177 |
| 2008/0105384 A1 | 5/2008 | Eckstein | |

FOREIGN PATENT DOCUMENTS

| | | |
|---|---|---|
| JP | 2849235 | 11/1998 |
| JP | 2849235 B2 | 1/1999 |
| JP | 3161676 | 2/2001 |
| JP | 2001269368 | 10/2001 |
| JP | 3269719 | 1/2002 |
| JP | 2003299691 | 10/2003 |
| WO | 9700654 | 1/1997 |
| WO | 0145611 A1 | 6/2001 |

OTHER PUBLICATIONS

Office Action dated Aug. 20, 2013, corresponds to Chinese patent application No. 201080044884.0.

Extended European Search Report dated Aug. 19, 2013, corresponds to European patent application No. 10822093.0.

International Search Report for PCT/JP2010/067658 mailed Nov. 22, 2010.

Office Action mailed Jul. 2, 2013 corresponds to Japanese patent application No. 2009-233837.

Office Action dated Jul. 9, 2014, corresponds to Eurasian patent application No. 201200386/31.

Office Action issued Jun. 4, 2014, corresponds to Chinese patent application No. 201080044884.0.

* cited by examiner

FIG.13
(A)
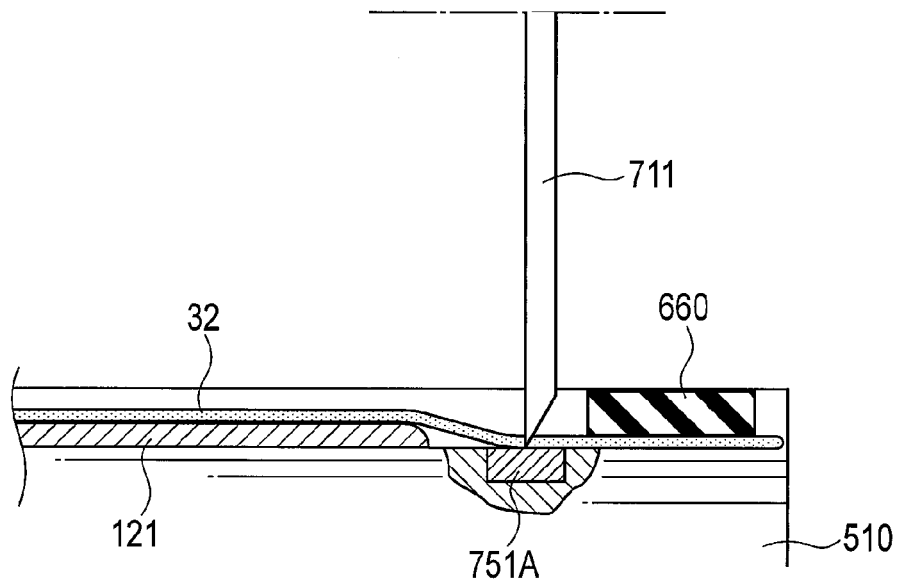
(B)
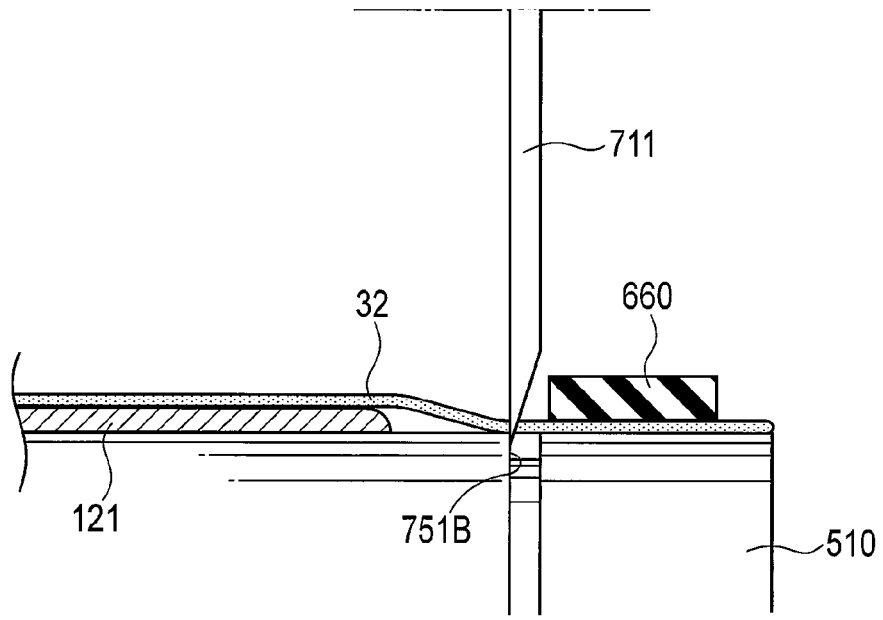

APPARATUS FOR MANUFACTURING A DISPOSABLE WEARING ARTICLE

RELATED APPLICATIONS

The present application is a National Phase of International Application Number PCT/JP2010/067658, filed Oct. 7, 2010, and claims priority from, Japanese Application Number 2009-233837, filed Oct. 7, 2009.

TECHNICAL FIELD

The present invention relates to an apparatus for manufacturing a disposable wearing article, provided with an oscillating mechanism for disposing an elastic member on a sheet-like continuous body such as a web.

BACKGROUND ART

In disposable wearing articles such as a disposable diaper and disposable pants, there is widely used a structure in which so-called leg gathers are arranged so that leg girth portions corresponding to groins of the wearer fit with the disposable wearing article. In such a disposable wearing article, the leg gathers are stretched according to the shape of the leg girth portions or movement of the wearer, and thus, the fit to the wearer (in particular, to the leg girth portions) can be secured.

Generally, as methods for manufacturing a leg gather according to the shape of the leg girth portions, there is known that by which a thin, long elastic member (e.g., filament-like rubber) is disposed in an expanded state on a sheet-like continuous body, such as a web, which is conveyed. Specifically, by means of an oscillating mechanism feeding the elastic member, which is oscillated (reciprocated), along a crossing direction (CD) crossing a conveyance direction (machine direction: MD) of the continuous body, the elastic member can be disposed on the conveyed continuous body in a waveform having a predetermined amplitude. The continuous body onto which the elastic member disposed in a waveform is bonded is cut into product sizes. The shape of the elastic member comes to fit the shape of the leg girth portions of the wearer.

Disposable pants for light incontinence, for example, are demanded to provide the fitting feeling that a wearer can feel when wearing underwear, and thus, a much improved sense of the "fit" is preferable. Therefore, there is known a method in which one portion of the elastic member disposed in a waveform by the oscillating mechanism is disposed to be deviated further outside a width-direction end of the continuous body (see Patent Document 1). Such a method facilitates the disposing of the elastic member to the entire region of the leg girth portions or realization of the shape of the elastic member that further fits the shape of the leg girth portions. It is noted that in this case, the elastic member not disposed on the continuous body is cut and removed in a downstream step.

However, the aforementioned conventional method of manufacturing a leg gather has the following problems: That is, there is a problem that when one portion of the elastic member is disposed and deviated from the continuous body, the elastic member neither disposed nor bonded on the continuous body instantaneously attempts to contract, resulting in a cause of a quality failure such as a wrinkle.

Another problem is that although the elastic member not disposed on the continuous body needs to be cut and removed in a downstream step, the expanded elastic member attempts to contract at the time of cutting, and thus, it is difficult to cut, again resulting in the cause of a quality failure.

PRIOR ART DOCUMENT

Patent Document

Patent Document 1: Japanese Patent Application Laid-open No. H04-317650 (pages 8 to 9, FIG. 4)

SUMMARY OF INVENTION

An apparatus for manufacturing a disposable wearing article (diaper manufacturing apparatus 500) according to a first aspect is equipped with an oscillating mechanism (oscillating mechanism 520) feeding an elastic member (e.g., a leg gather 32), which is being oscillated, along a crossing direction (crossing direction: CD) crossing a conveyance direction (mechanical direction: MD) of a sheet-like continuous body (e.g., a top-sheet continuous body 121) and disposing one portion of the expanded elastic member onto the continuous body to which an adhesive is applied. The apparatus for manufacturing a disposable wearing article includes: an outer holding mechanism (outer holding mechanism 650) at least holding the elastic member disposed in a predetermined waveform by the oscillating mechanism; and a cutting mechanism (cutting mechanism 540) having a blade section at least cutting the elastic member held by the outer holding mechanism, in which the outer holding mechanism holds, out of a region formed in the predetermined waveform by the elastic member, an outer end region (outer end region OT) which includes an outer end (outer end 32e) of the elastic member in the crossing direction and to which the adhesive is not applied, and the blade section is disposed inside, relative to the crossing direction, the outer end region held by the outer holding mechanism.

BRIEF DESCRIPTION OF DRAWINGS

FIG. 1 is an exploded perspective view showing a diaper 1 according to a first embodiment.
FIG. 2 is a perspective view showing a diaper manufacturing apparatus 500 according to the first embodiment.
FIG. 3 is a side view showing the diaper manufacturing apparatus 500, as seen from an F3 direction of FIG. 2.
FIG. 4 is a perspective view showing a vicinity of a holding mechanism 530 according to the first embodiment.
FIG. 5 is a cross-sectional view showing one portion of the diaper manufacturing apparatus 500 along a line F5-F5 in FIG. 4.
FIG. 6 is a schematic plan view showing the diaper manufacturing apparatus 500 as seen from an F6 direction in FIG. 4.
FIG. 7 is a perspective view showing a vicinity of a cutting mechanism 540 according to the first embodiment.
FIG. 8 is a cross-sectional view showing one portion of the diaper manufacturing apparatus 500 along a line F8-F8 in FIG. 7.

FIG. 9 is a schematic plan view showing the diaper manufacturing apparatus 500 as seen from an F9 direction in FIG. 7.

FIG. 10 is a flowchart for explaining a method for manufacturing the diaper 1 according to the first embodiment.

FIG. 11 is a perspective view showing a diaper manufacturing apparatus 500A according to a second embodiment.

FIG. 12 is a side view showing the diaper manufacturing apparatus 500A as seen from an F12 direction in FIG. 11.

[FIG. 13]

FIGS. 13 (A) and 13 (B) are a cross-sectional view showing one portion of the diaper manufacturing apparatus 500A along a line F13-F13 in FIG. 11.

DESCRIPTION OF EMBODIMENTS

Subsequently, embodiments of an apparatus for manufacturing a disposable wearing article according to the present invention will be explained with reference to the diagrams. Specifically, a first embodiment, a second embodiment, and other embodiments will be explained.

In the following description of the diagrams, the identical or similar portions are assigned the identical or similar numerals. However, it should be noted that the diagrams are schematic and ratios of the respective dimensions do not justify the actual ones.

Therefore, the specific dimensions, etc., should be determined in consideration of the following explanations. Moreover, it is needless to say that relations and ratios among the respective dimensions differ among the diagrams.

[First Embodiment]
(Configuration of Diaper)

Figure 1:
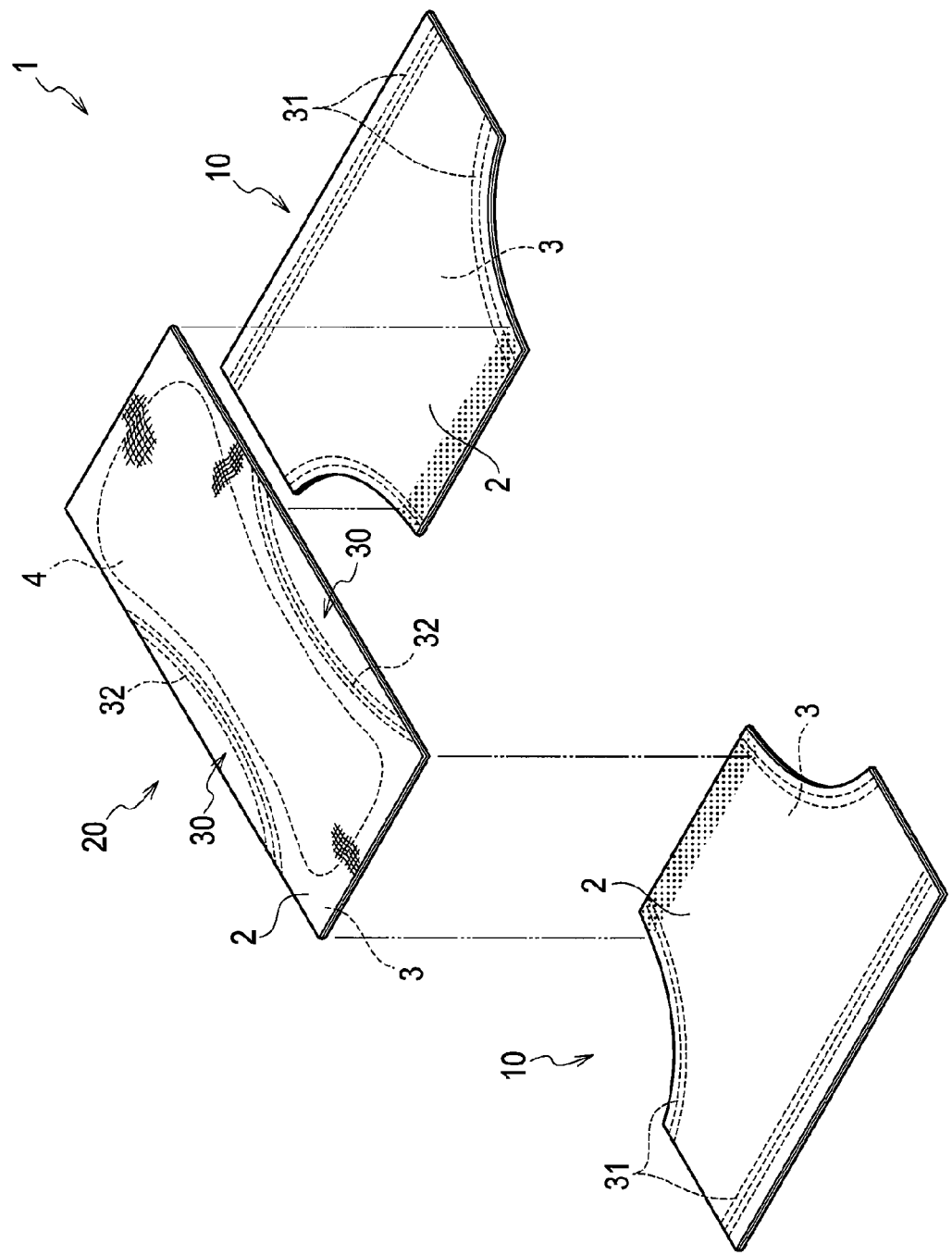
[FIG. 1]

First, the configuration of a diaper 1 manufactured by a diaper manufacturing apparatus 500 according to a first embodiment will be explained with reference to diagrams. In the first embodiment, as a disposable wearing article, a disposable diaper (hereinafter, simply called "diaper 1") is used. FIG. 1 is an exploded perspective view showing the diaper 1 according to the first embodiment.

As shown in FIG. 1, the diaper 1 is configured of a top sheet 2, a back sheet 3, and an absorber 4. The top sheet 2 has a surface that comes into contact with the skin of the wearer. The top sheet 2 is formed of a liquid-permeable sheet such as a hydrophilic nonwoven cloth or fabric, an aperture plastic film, and an aperture hydrophobic nonwoven cloth. The back sheet 3 is arranged opposite the top sheet 2, as seen from the absorber 4. The back sheet 3 is formed of a liquid-impermeable sheet such as polyethylene. The absorber 4 is arranged between the top sheet 2 and the back sheet 3. The absorber 4 is formed of a mixed powder of a ground pulp, highly-absorbent polymer, etc., and a covering material such as a tissue covering the mixed powder.

The diaper 1 is formed by combining: a pair of waistline sections 10 corresponding to the waist of the wearer; and an inner leg section 20 that is positioned between the pair of the waistline sections 10 and that corresponds to an inner leg of the wearer.

In the waistline sections 10, a thin, long waist gather 31 (elastic member) corresponding to the waist of the wearer is arranged. The waist gather 31 is disposed between the top sheet 2 and the back sheet 3 in an expanded state. The waist gather 31 is formed of filament-like rubber, plain rubber, ribbon-like rubber, a ribbon-like stretchable sheet, etc.

On the other hand, in the inner leg section 20, a pair of leg girth portions 30 corresponding to the groins of the wearer is formed. In the pair of leg girth portions 30, thin, long leg gathers 32 (elastic members) corresponding to the groin of the wearer are respectively arranged. The leg gathers 32 are disposed between the top sheet 2 and the back sheet 3 in an expanded state. The leg gathers 32 are formed of filament-like rubber, plain rubber, ribbon-like rubber, a ribbon-like stretchable sheet, etc.

(Overview of Configuration of Diaper Manufacturing Apparatus)

Figure 2:
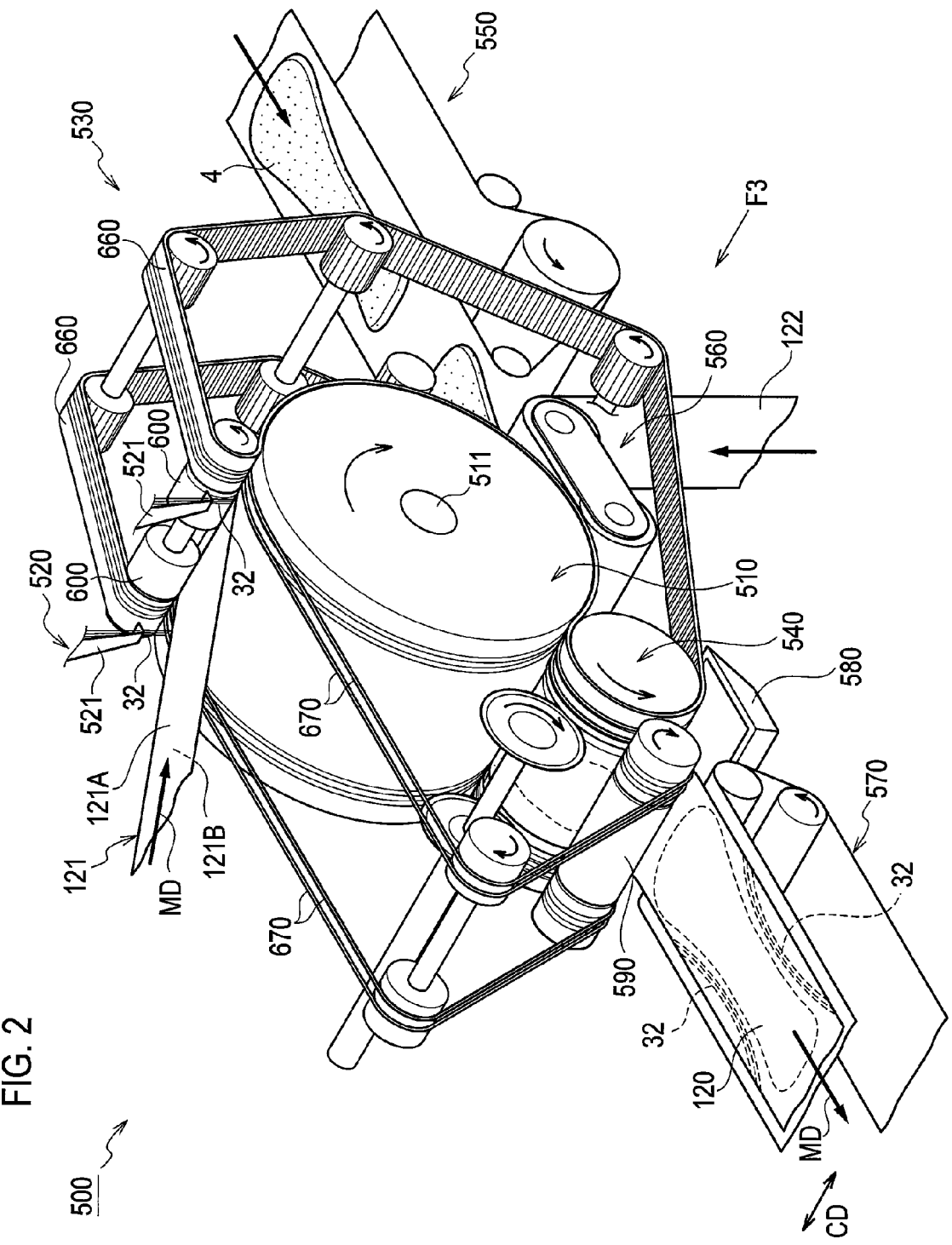
[FIG. 2]
Figure 3:
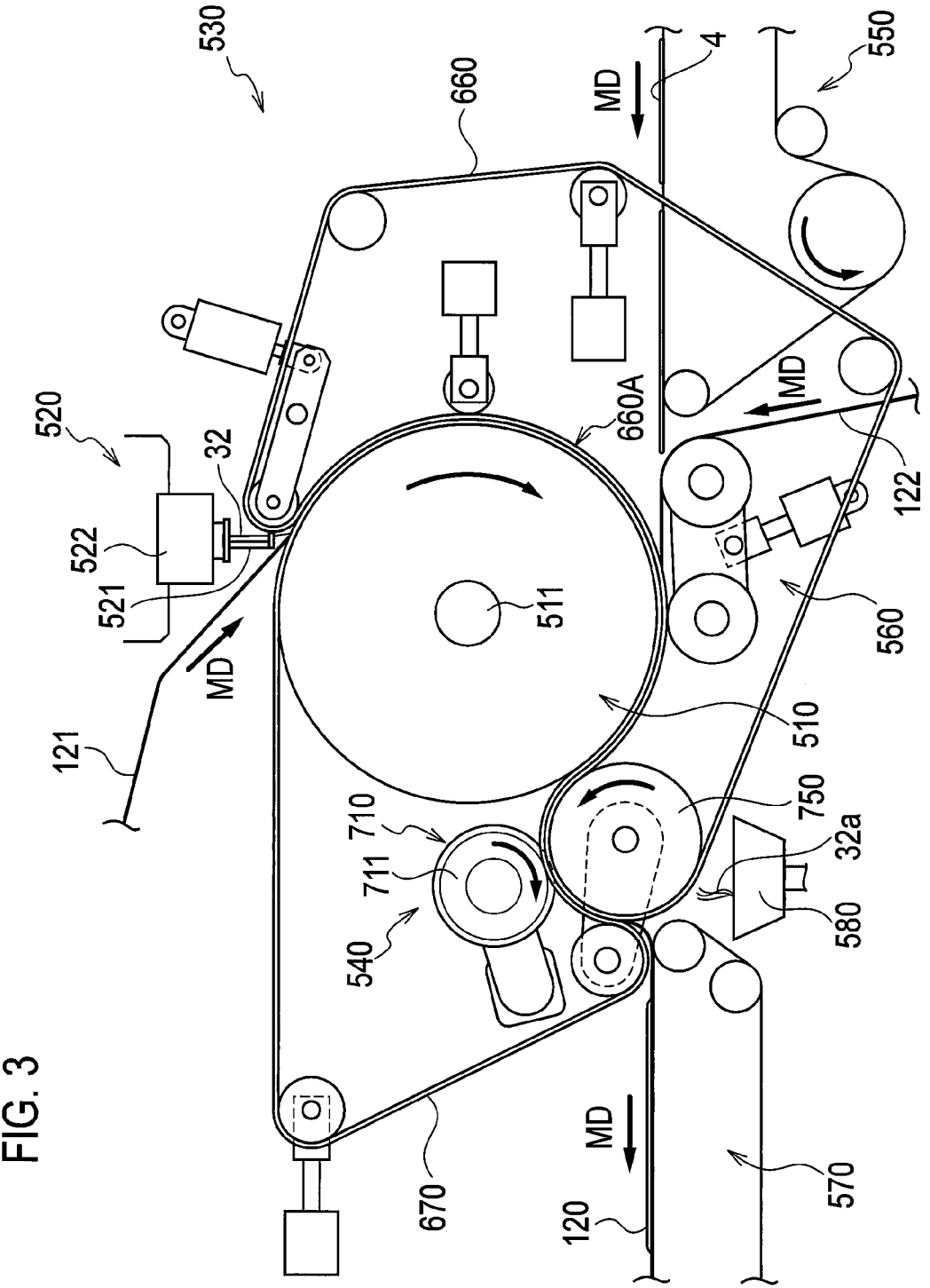
[FIG. 3]

Subsequently, an overview of the configuration of the diaper manufacturing apparatus 500 (apparatus for manufacturing a disposable wearing article) for manufacturing the inner leg section 20 of the aforementioned diaper 1 will be explained with reference to diagrams. FIG. 2 is a perspective view showing the diaper manufacturing apparatus 500 according to the first embodiment. FIG. 3 is a side view showing the diaper manufacturing apparatus 500, as seen from an F3 direction of FIG. 2.

As shown in FIG. 2 and FIG. 3, the diaper manufacturing apparatus 500 includes: a drum main body 510; an oscillating mechanism 520; a holding mechanism 530; a cutting mechanism 540; an absorber disposing mechanism 550; a backsheet pressing mechanism 560; a sheet conveyance mechanism 570; and a rubber collection mechanism 580.

The drum main body 510 is capable of rotating along a conveyance direction (hereinafter, a machine direction: MD) of a sheet-like top-sheet continuous body 121 in which the top sheets 2 are continued. The drum main body 510 conveys the top-sheet continuous body 121 along the machine direction MD.

An axial core 511 of the drum main body 510 is arranged along a crossing direction CD crossing the machine direction MD. The top-sheet continuous body 121 in which the leg gathers 32 are disposed runs along the outer circumferential surface of the drum main body 510.

The oscillating mechanism 520 is disposed above the drum main body 510. The oscillating mechanism 520 feeds the leg gathers 32 corresponding to the leg girth portions 30 of the wearer while oscillating (reciprocating) the leg gathers 32 along the crossing direction CD. Moreover, the oscillating mechanism 520 disposes at least one portion of the expanded leg gathers 32 onto the top-sheet continuous body 121 on which an adhesive is applied. The result is that the oscillating mechanism 520 is capable of disposing the leg gathers 32 onto the conveyed top-sheet continuous body 121 in a waveform having a predetermined amplitude (SW in FIG. 6).

In this case, the waveform having a predetermined amplitude means a shape (the shortest distance L1 or the longest distance L2 in FIG. 6) in which a distance along the crossing direction CD of a pair of leg gathers 32 changes in a predetermined cycle (e.g., a cycle of product size) relative to the machine direction MD. It is noted that the shape is not necessarily a waveform, and can be zigzag.

The oscillating mechanism 520 is configured of an arm member 521 and a motor 522 (see FIG. 3). The arm member 521 guides the leg gathers 32 along the crossing direction CD. The motor 522 oscillates the arm member 521 along the crossing direction CD.

The holding mechanism 530 at least holds the leg gathers 32 disposed in a predetermined waveform by the oscillating mechanism 520, toward the outer circumferential surface of the drum main body 510. The cutting mechanism 540 cuts at least the leg gathers 32 held by the holding mechanism 530 (outer holding mechanism 650 described later). It is noted that the holding mechanism 530 and the cutting mechanism 540 will be described in detail later.

In the top-sheet continuous body 121 in which the leg gathers 32 are disposed, the absorber disposing mechanism 550 is configured of a belt conveyor in which the absorbers 4 are disposed for each predetermined interval in the machine direction MD. The absorber disposing mechanism 550 is disposed downstream, relative to the machine direction MD, of the oscillating mechanism 520 and disposed upstream, relative to the machine direction MD, of the cutting mechanism 540.

The back-sheet pressing mechanism 560 is configured of a roll mechanism pressing the sheet-like back-sheet continuous body 122 in which the back sheets 3 are continued in the top-sheet continuous body 121 in which the absorber 4 is disposed. The back-sheet pressing mechanism 560 is disposed downstream, relative to the machine direction MD, of the absorber disposing mechanism 550 and disposed upstream, relative to the machine direction MD, of the cutting mechanism 540.

The sheet conveyance mechanism 570 is configured of a belt conveyor conveying the top-sheet continuous body 121 (inner-leg-section continuous body 120 described later) in which one portion of the leg gathers 32 is cut by the cutting mechanism 540 to a downstream process. The sheet conveyance mechanism 570 is disposed downstream, relative to the machine direction MD, of the cutting mechanism 540.

The rubber collection mechanism 580 absorbs, collects, and abandons unnecessary rubber 32a, out of the leg gathers 32 cut by the cutting mechanism 540. The rubber collection mechanism 580 is disposed below the cutting mechanism 540.

(Configuration of Holding Mechanism)

Figure 4:
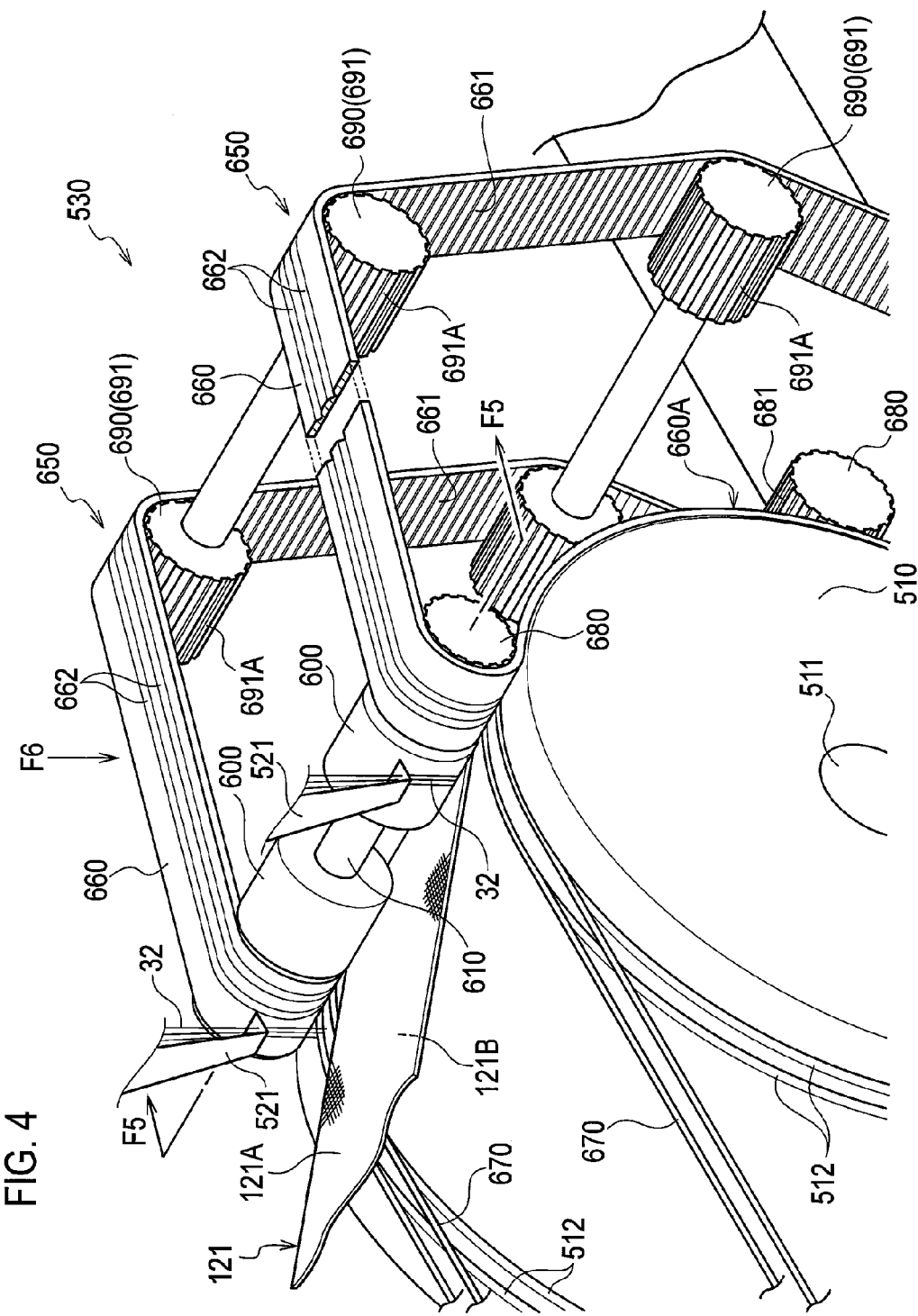
[FIG. 4]
Figure 5:
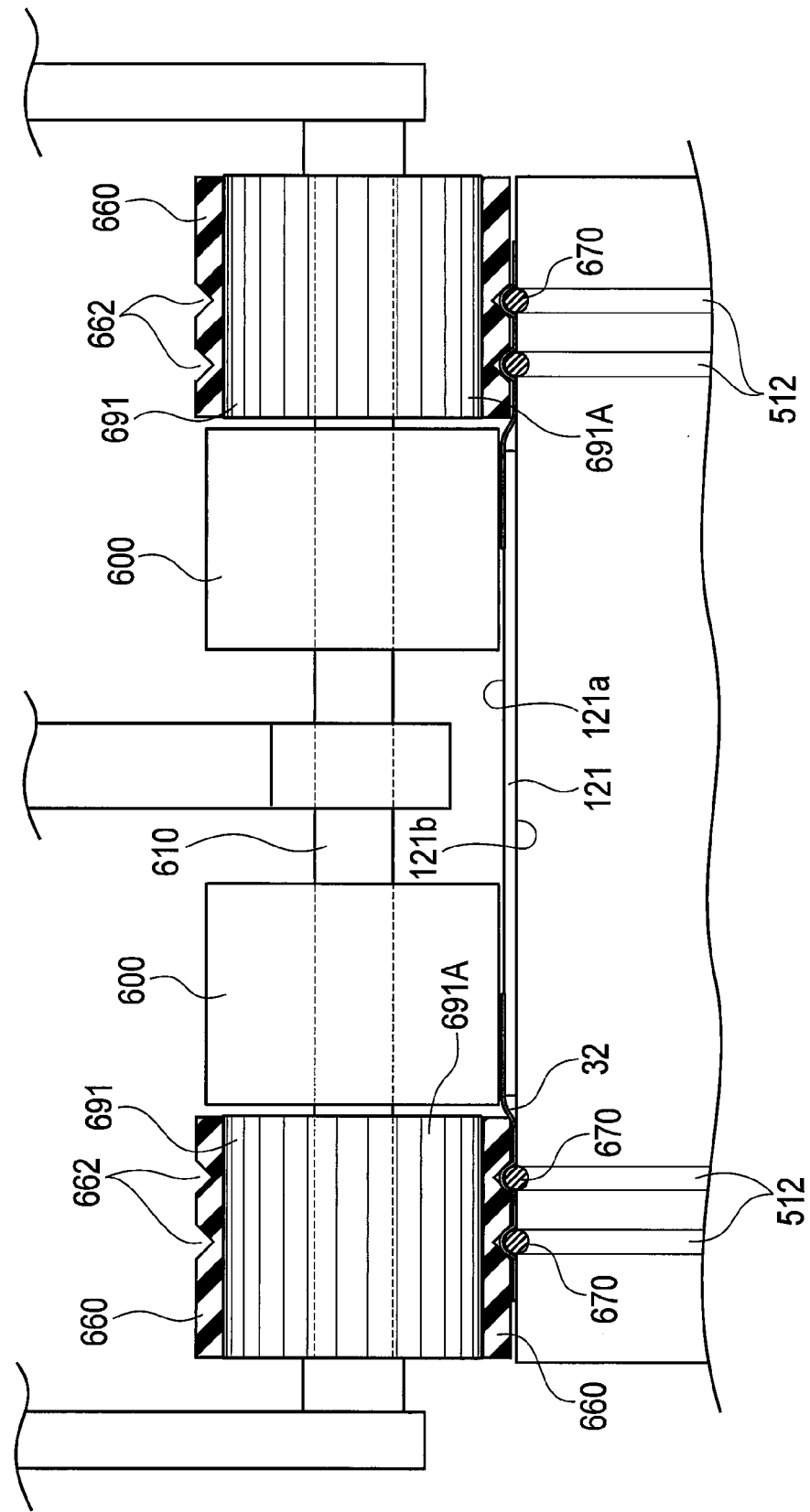
[FIG. 5]
Figure 6:
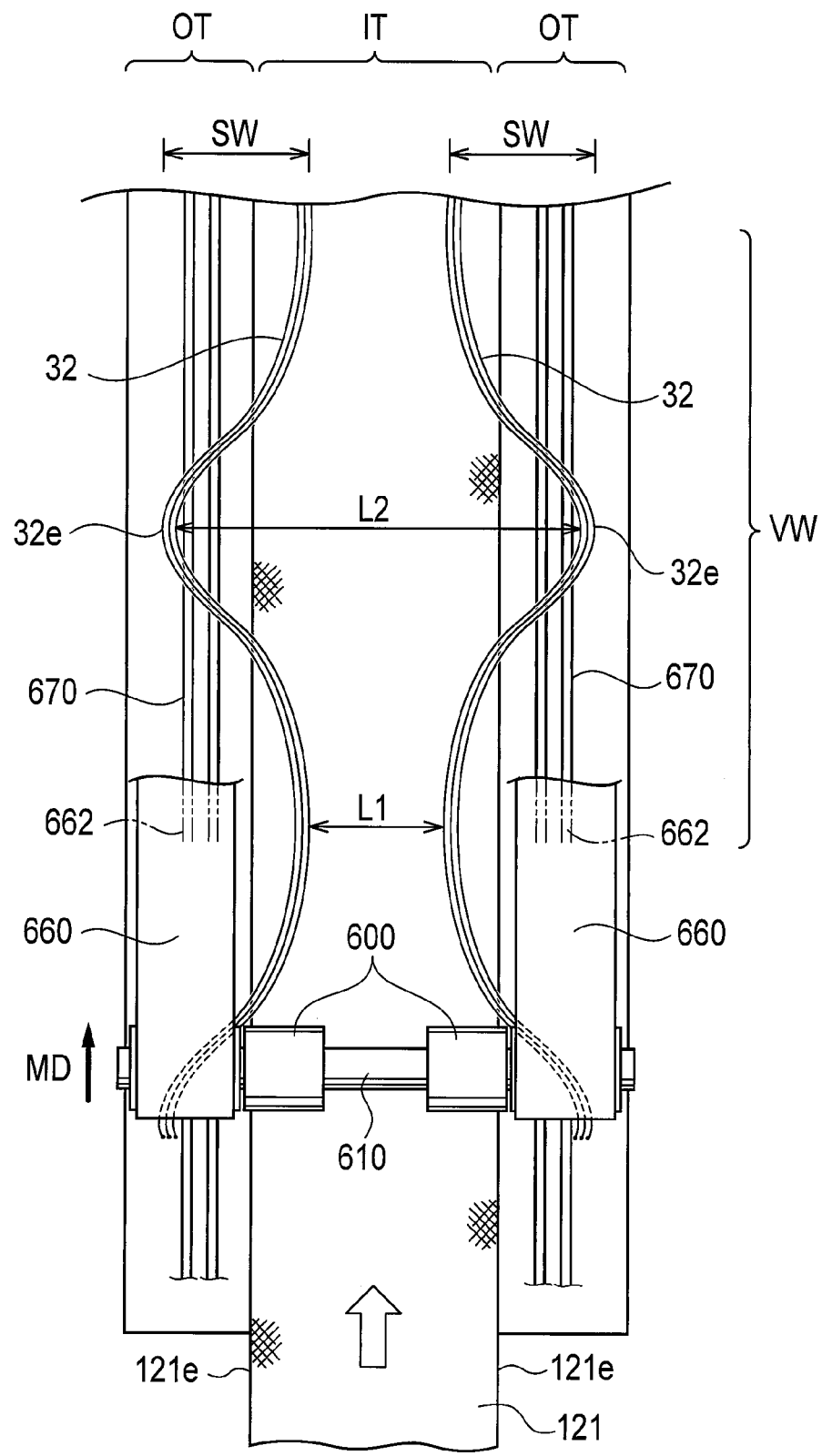
[FIG. 6]

Subsequently, the configuration of the holding mechanism 530 according to the first embodiment will be explained with reference to FIG. 4 to FIG. 6. FIG. 4 is a perspective view showing a vicinity of the holding mechanism 530 according to the first embodiment. FIG. 5 is a cross-sectional view showing one portion of the diaper manufacturing apparatus 500 along a line F5-F5 in FIG. 4. FIG. 6 is a schematic plan view showing the diaper manufacturing apparatus 500, as seen from an F6 direction of FIG. 4.

As shown in FIG. 4 to FIG. 6, the holding mechanism 530 is configured of an inner holding mechanism 600 and an outer holding mechanism 650.

The inner holding mechanism 600 holds one side surface 121A of the top-sheet continuous body 121 in which the leg gathers 32 are disposed in a predetermined waveform by the oscillating mechanism 520, toward the outer circumferential surface of the drum main body 510. That is, the inner holding mechanism 600 holds the leg gathers 32 on the top-sheet continuous body 121 in a state where the leg gathers 32 are held in a predetermined waveform.

In the first embodiment, as shown in FIG. 6, the inner holding mechanism 600 holds an inner region IT located inside the crossing direction CD, out of a region formed in a predetermined waveform by the leg gathers 32. It is noted that the inner region IT indicates an inner side, relative to the crossing direction CD, of a width-direction end 121e (outer end) of the top-sheet continuous body 121 in the crossing direction CD. Moreover, the inner region IT is a region in which an adhesive is applied to the top-sheet continuous body 121, i.e., a region in which the leg gathers 32 are bonded to the top-sheet continuous body 121.

The inner holding mechanism 600 is disposed inside, relative to the crossing direction CD, the outer holding mechanism 650, and disposed above the drum main body 510 and disposed downstream, relative to the machine direction MD, of the oscillating mechanism 520. The inner holding mechanism 600 is configured of a pair of roll mechanisms. An axial core 610 of the inner holding mechanism 600 is arranged substantially parallel to the axial core 511 of the drum main body 510.

The outer holding mechanism 650 holds only the leg gathers 32 disposed in a predetermined waveform, toward the outer circumferential surface of the drum main body 510. That is, the outer holding mechanism 650 holds the leg gathers 32 deviated from the top-sheet continuous body 121 in a state where the leg gathers 32 are held in a predetermined waveform.

In the first embodiment, as shown in FIG. 6, the outer holding mechanism 650 holds an outer end region OT including an outer end 32e of the leg gathers 32 in the crossing direction CD, out of the region formed in a predetermined waveform by the leg gathers 32. It is noted that the outer end region OT indicates an outer side, relative to the crossing direction CD, of the width-direction end 121e of the top-sheet continuous body 121. Moreover, the outer end region OT is a region in which the adhesive is not applied to the top-sheet continuous body 121, i.e., a region in which the leg gathers 32 are not bonded to the top-sheet continuous body 121 (in this embodiment, a region consisting only of the leg gathers 32).

In this case, in one waveform (WV in FIG. 6) deviated from the top-sheet continuous body 121, the outer holding mechanism 650 preferably holds at least two or more holding points of the leg gathers 32, toward the outer circumferential surface of the drum main body 510.

The outer holding mechanism 650 is disposed outside, relative to the crossing direction CD, the inner holding mechanism 600. The outer holding mechanism 650 is disposed along the machine direction MD between the inner holding mechanism 600 and the cutting mechanism 540. That is, the outer holding mechanism 650 keeps on holding the leg gathers 32 located in the outer end region OT until at least the leg gathers 32 are cut.

The outer holding mechanism 650 includes: a pair of endless flat belts 660 (endless belts); a plurality of endless round belts 670 (intermediate endless belts); a plurality of belt-holding roll mechanisms 680; and a plurality of belt-guiding roll mechanisms 690.

On the surface 121A of the top-sheet continuous body 121 in which the pair of leg gathers 32 are disposed, the flat belts 660 hold the pair of leg gathers 32 deviated from the top-sheet continuous body 121, toward the outer circumferential surface of the drum main body 510. The flat belts 660 are formed by using an elastic member (e.g., a rubber material).

The flat belts 660 each have an arc section 660A (see FIG. 3 and FIG. 4) that can rotate along the machine direction MD and that forms an arc shape along the outer circumferential surface of the drum main body 510. On a surface not contacting the leg gathers 32 of the flat belts 660, there are formed a plurality of tooth-like convex sections 661 meshing with convex sections 691A of flat-belt guiding rolls 691 described later. The convex sections 661 are disposed in the machine direction MD for each predetermined interval. That is, the flat belts 660 are each configured of a timing belt (toothed belt).

The shape of the cross section along a shorter direction of the flat belts 660 is a polygon in which the length of a side along the crossing direction CD is longer than the length of any other side. In the first embodiment, the cross section along the shorter direction of the flat belts 660 is rectangular.

On a top surface of the flat belts 660 facing the round belts 670 (i.e., a surface contacting the top-sheet continuous body 121), there are formed concave sections 662 with which at least one portion of the round belts 670 is fitted via the leg gathers 32. That is, one portion of the leg gathers 32 and one portion of the round belts 670 enter into the concave sections 662. The concave sections 662 are arranged continuously along a rotation direction of the flat belts 660. The depth of the concave section 662 is shallower than a height along a depth direction of the concave sections 662 of the round belts 670, i.e., a thickness of the round belt 670 (see FIG. 5).

The round belts 670 are disposed between the drum main body 510 and the flat belts 660. Between the round belts 670 and the flat belts 660, the pair of leg gathers 32 are sandwiched. Two round belts 670 are arranged on one side of the leg gathers 32 and the other side of the leg gathers 32, respectively. The round belts 670 are formed by using an elastic member (e.g., a rubber material).

The thickness of the round belts 670 is thinner than the length (width) along the crossing direction CD of the flat belts 660. The shape of the cross section along a shorter direction of the round belts 670 is circular. The round belts 670, together with one portion of the leg gathers 32, enter into the concave sections 662 thereby to hold the leg gathers 32.

In this case, on the outer circumferential surface of the drum main body 510, concave sections 512 (drum-side concave sections) into which at least one portion of the round belts 670 enters are formed. The concave sections 512 are arranged continuously along a rotation direction of the drum main body 510. The depth of the concave sections 512 is shallower than a height along a depth direction of the concave sections 512 of the round belts 670, i.e., the thickness of the round belts 670.

The belt-holding roll mechanisms 680 hold the flat belts 660 and the round belts 670, toward the outer circumferential surface of the drum main body 510. The belt-holding roll mechanisms 680 are disposed outside, relative to the crossing direction CD, the inner holding mechanism 600.

On the outer circumferential surface of the belt-holding roll mechanisms 680, there are formed tooth-like convex sections 681 meshing among the convex sections 661 of the flat belts 660 (see FIG. 4). The convex sections 681 are disposed in a rotation direction of the belt-holding roll mechanisms 680 for each predetermined interval.

It is noted that out of a plurality of belt-holding roll mechanisms 680, at least one belt-holding roll mechanism 680 may be a roll mechanism capable of adjusting an intensity to hold the flat belts 660 and the round belts 670 down on the outer circumferential surface of the drum main body 510.

The belt-guiding roll mechanisms 690 guide circling of the flat belts 660 and the round belts 670. The belt-guiding roll mechanisms 690 include a plurality of flat-belt guiding rolls 691 and a plurality of round-belt guiding rolls 692.

A plurality of flat-belt guiding rolls 691 are arranged on a circling path of the flat belts 660. On the outer circumferential surface of the flat-belt guiding rolls 691, tooth-like convex sections 691A meshing among the convex sections 661 of the flat belts 660 are formed. The convex sections 691A are disposed in a rotation direction of the flat-belt guiding rolls 691 for each predetermined interval. It is noted that out of the plurality of flat-belt guiding rolls 691, at least one of the flat-belt guiding rolls 691 may be a roll mechanism capable of adjusting a tension of the flat belts 660.

On the other hand, a plurality of round-belt guiding rolls 692 are arranged on a circling path of the round belts 670. On the outer circumferential surface of the round-belt guiding rolls 692, there are formed concave sections 692A into which at least one portion of the round belts 670 enters (see FIG. 7). The concave sections 692A are arranged continuously along a rotation direction of the round-belt guiding rolls 692. It is noted that out of the plurality of round-belt guiding rolls 692, at least one round-belt guiding roll 692 may be a roll mechanism capable of adjusting the tension of the round belts 670.

(Configuration of Cutting Mechanism)

Figure 7:
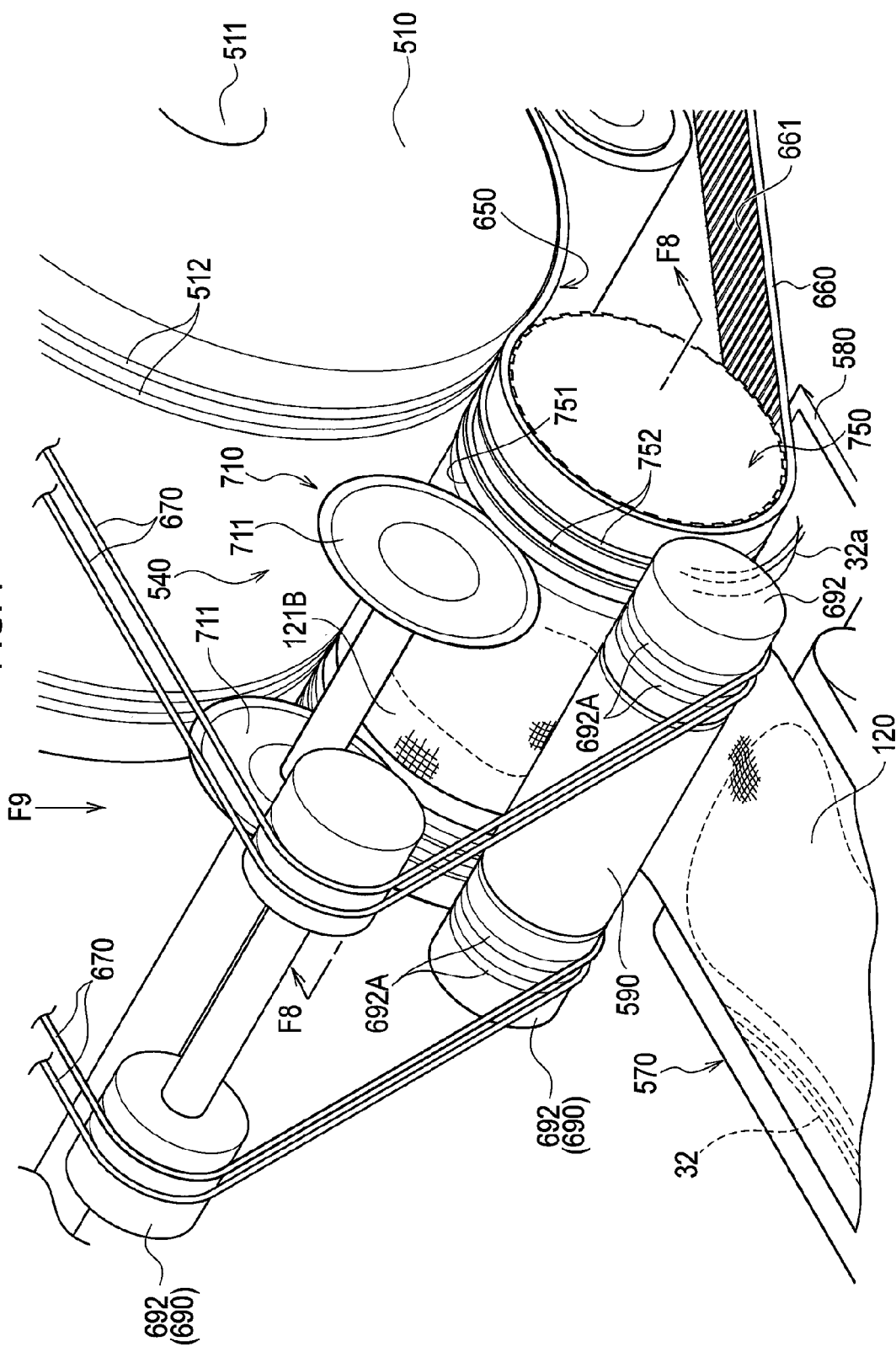
[FIG. 7]
Figure 8:
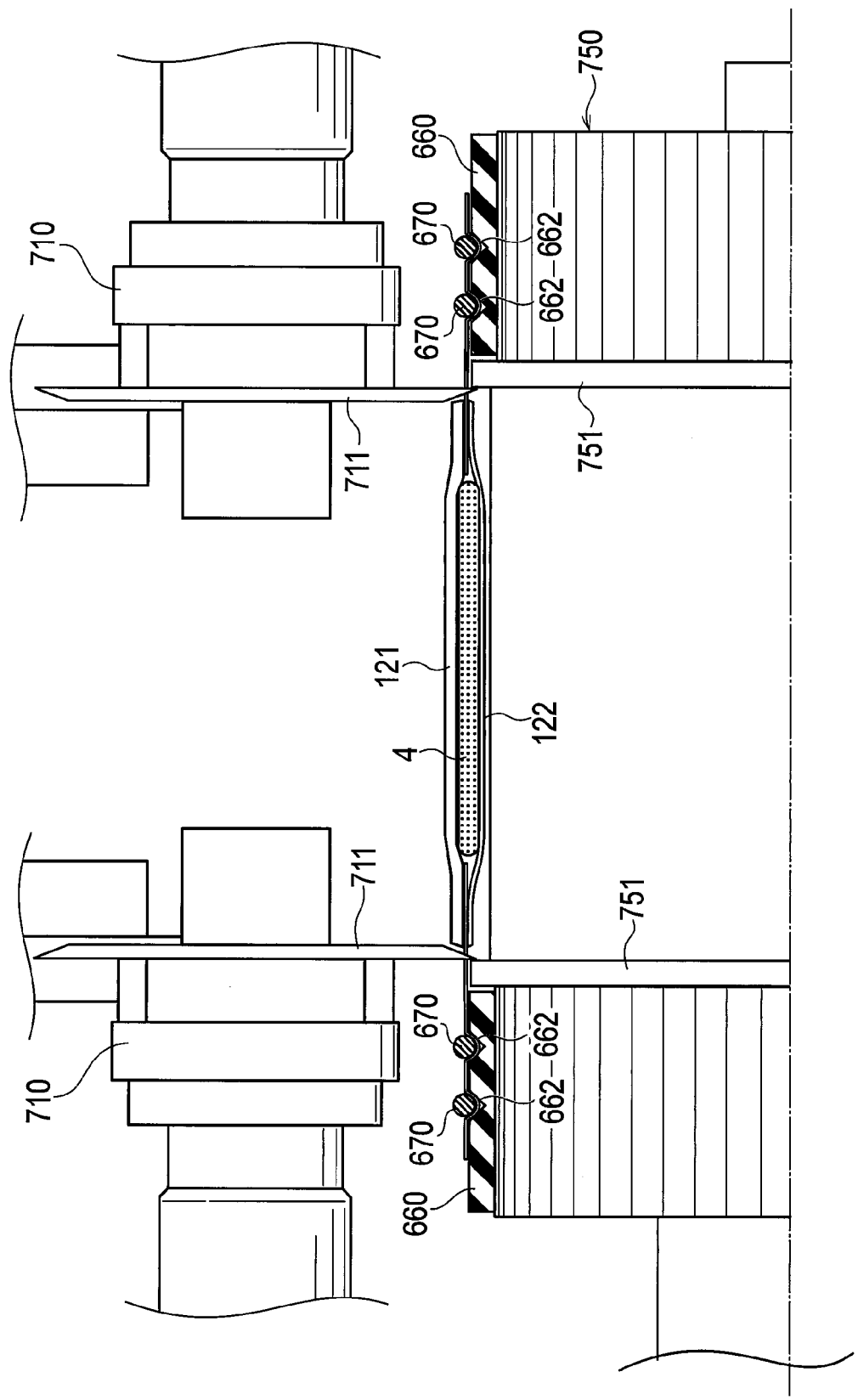
[FIG. 8]
Figure 9:
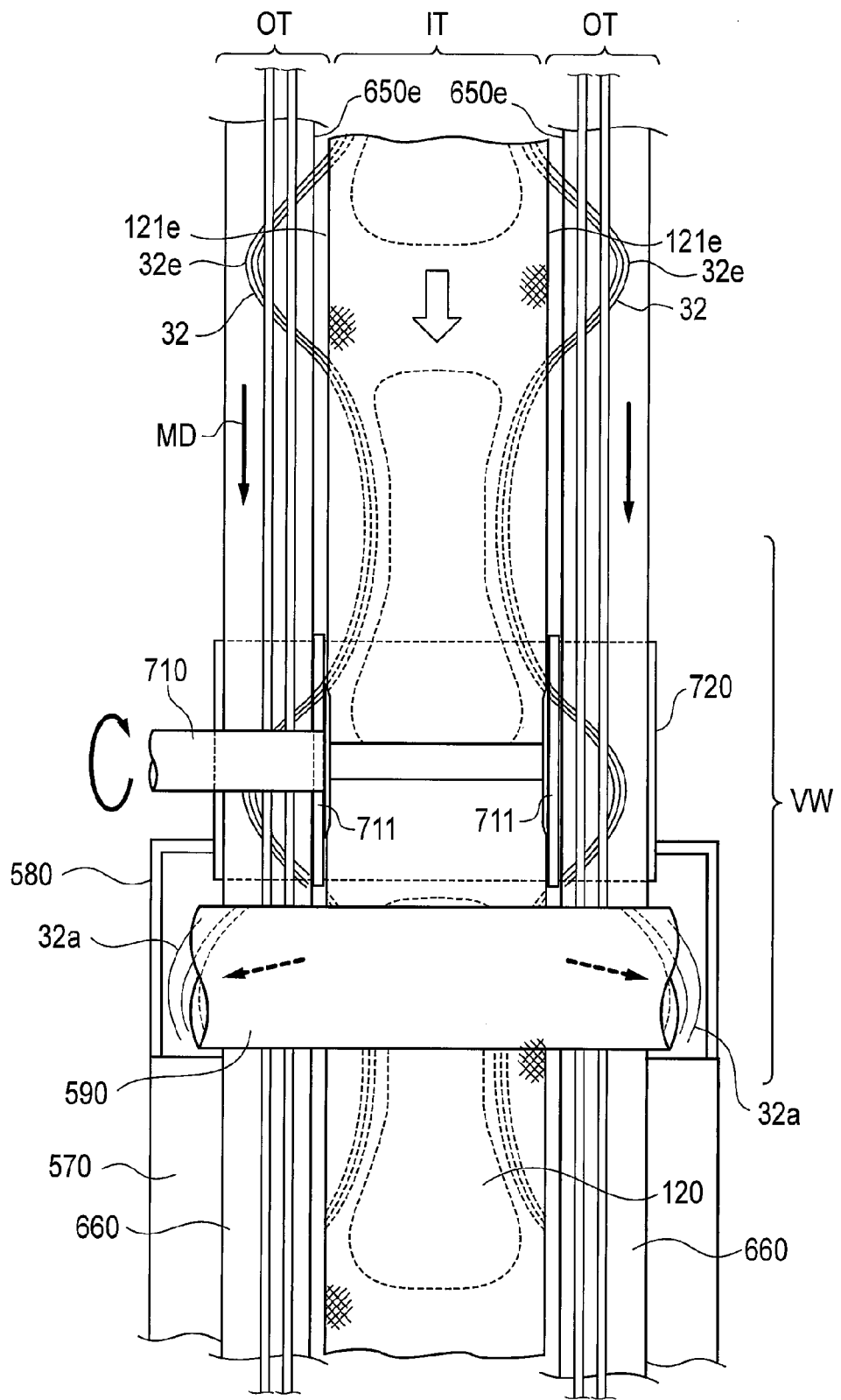
[FIG. 9]

Subsequently, the configuration of the cutting mechanism 540 according to the first embodiment will be explained with reference to FIG. 7 to FIG. 9. FIG. 7 is a perspective view showing a vicinity of the cutting mechanism 540 according to the first embodiment. FIG. 8 is a cross-sectional view showing one portion of the diaper manufacturing apparatus 500 along a line F8-F8 in FIG. 7. FIG. 9 is a schematic plan view showing the diaper manufacturing apparatus 500, as seen from an F9 direction of FIG. 7.

As shown in FIG. 7 to FIG. 9, the cutting mechanism 540 is disposed below the drum main body 510 and downstream of the drum main body 510. That is, the cutting mechanism 540 is disposed downstream, relative to the machine direction MD, of the absorber disposing mechanism 550 and the backsheet pressing mechanism 560.

The cutting mechanism 540 has a blade section cutting the leg gathers 32 held by the flat belts 660 and the round belts 670. The blade section is configured of an upper blade roll 710 and a lower blade roll 750.

In the upper blade roll 710, an upper blade 711 (first blade) capable of rotating along the machine direction MD is arranged. The upper blade 711 comes into contact with the leg gathers 32 on the other surface 121B opposite the one surface 121A of the top-sheet continuous body 121, and cuts the leg gathers 32. The upper blade 711 is in a disc shape capable of rotating along the machine direction MD.

In the lower blade roll 750, a lower blade 751 (second blade) capable of rotating along the machine direction MD is arranged. The lower blade 751 comes into contact with the leg gathers 32 on the one surface 121A of the top-sheet continuous body 121, and cuts the leg gathers 32. The lower blade 751 is formed along the outer circumferential surface of the lower blade roll 750 in a manner to contact at least one portion of the upper blade 711.

The upper blade 711 and the lower blade 751 are disposed inside, relative to the crossing direction CD, the outer end region OT held by the outer holding mechanism 650. In the embodiment, as shown in FIG. 9, the upper blade 711 and the lower blade 751 are disposed between a width-direction end 121e of the top-sheet continuous body 121 by the outer holding mechanism 650 and an inner end 650e of the outer holding mechanism 650 in the crossing direction CD in which the leg gathers 32 are held by the outer holding mechanism 650.

As a result of overlapping a rim or one portion of the lower blade 751 (see FIG. 8), a rim or one portion of the upper blade 711 sandwiches and cuts at least the leg gathers 32. Thereby, the leg gathers 32 deviated from the top-sheet continuous body 121 are cut.

In this case, downstream of the cutting mechanism 540, a sheet guiding roll 590 guiding an inner-leg-section continuous body 120 (see FIG. 7 and FIG. 9) described later to the sheet conveyance mechanism 570 is attached. The sheet guiding roll 590 is attached to an axial core (not shown) of a round-belt guiding roll 692 that is closest to the cutting mechanism 540, out of the plurality of round-belt guiding rolls 692.

(Diaper Manufacturing Method)

Figure 10:
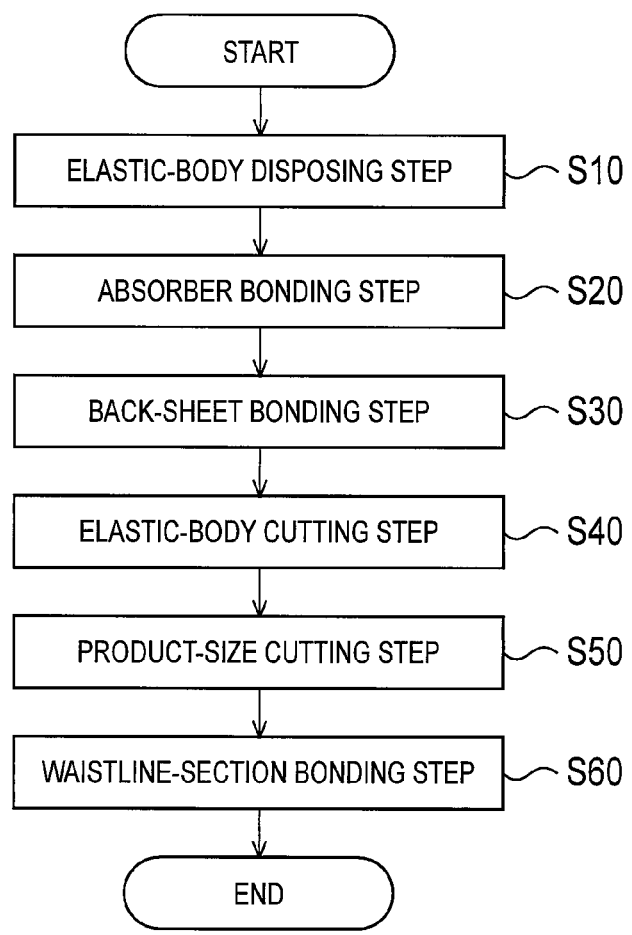
[FIG. 10]

Subsequently, a method for manufacturing the diaper 1 manufactured by using the aforementioned diaper manufacturing apparatus 500 will be explained with reference to diagrams. FIG. 10 is a flowchart for explaining the method for manufacturing the diaper 1 according to the first embodiment.

As shown in FIG. 10, the method for manufacturing the diaper 1 includes: an elastic-body disposing step S10; an absorber bonding step S20; a back-sheet bonding step S30; an elastic-body cutting step S40; a product-size cutting step S50; and a waistline-section bonding step S60.

In elastic-body disposing step S10, in the top-sheet continuous body 121 conveyed along the machine direction MD, the leg gathers 32 are disposed by the oscillating mechanism 520 in a waveform having a predetermined amplitude. At this time, the inner holding mechanism 600 holds the top-sheet continuous body 121 and the leg gathers 32 located at the inner region IT, toward the outer circumferential surface of the drum main body 510. Moreover, the outer holding mechanism 650 holds the leg gathers 32 located at the outer end region OT, toward the outer circumferential surface of the drum main body 510.

In this case, at the time of transportation from the drum main body 510 to the lower blade roll 750, the flat belts 660 and the round belts 670 work together to sandwich the leg gathers 32 located at the outer end region OT. Subsequently, after the transportation to the lower blade roll 750, the round belts 670 hold the leg gathers 32 located at the outer end region OT, toward the outer circumferential surface of the lower blade roll 750. That is, the outer holding mechanism 650 keeps on holding the leg gathers 32 located at the outer end region OT until at least the elastic-body cutting step S40 is ended (see FIG. 2 and FIG. 3).

In absorber bonding step S20, the absorber 4 is bonded by the absorber disposing mechanism 550 to the top-sheet continuous body 121 in the machine direction MD for each predetermined interval (see FIG. 2 and FIG. 3).

In back-sheet bonding step S30, the back-sheet continuous body 122 is bonded to the top-sheet continuous body 121 onto which the absorber 4 has been bonded by the back-sheet pressing mechanism 560 (see FIG. 2 and FIG. 3).

In elastic-body cutting step S40, the leg gathers 32 deviated from the top-sheet continuous body 121 onto which the back sheet continuous body 122 has been bonded are cut by the cutting mechanism 540. Specifically, the leg gathers 32 held by the flat belts 660 and the round belts 670 are cut between the width-direction end 121e of the top-sheet continuous body 121 and the inner end 650e of the outer holding mechanism 650. As a result, the inner-leg-section continuous body 120 is formed (see FIGS. 2, 3, and FIGS. 7, 9).

In product-size cutting step S50, the inner-leg-section continuous body 120 is cut along the crossing direction CD, and thereby, the inner leg section 20 of a product size (see FIG. 1) is formed.

In waistline-section bonding step S60, the aforementioned inner leg section 20 is bonded to the pair of previously formed waistline sections 10 (see FIG. 1). As a result, the diaper 1 is manufactured.

In the above-explained first embodiment, the outer holding mechanism 650 holds the leg gathers 32 disposed in a predetermined waveform by the oscillating mechanism 520. That is, the outer holding mechanism 650 holds one portion of the leg gathers 32 in a state where the one portion thereof is deviated externally of the width-direction end 121e of the top-sheet continuous body 121. This facilitates the disposing of the leg gathers 32 to the entire area of the leg girth portions 30 and the realization of the shape of the leg gathers 32 that fit the shape of the leg girth portions 30. As a result, the fit can be ensured to the wearer (in particular, to the leg girth portions 30).

Moreover, the outer holding mechanism 650 holds the leg gathers 32 disposed to be deviated from the top-sheet continuous body 121, i.e., the leg gathers 32 located at the outer end region OT. According thereto, it is possible to inhibit instantaneous contraction of one portion of the leg gathers 32 located at the outer end region OT. This eliminates a possibility that a wrinkle occurs due to the instantaneous contraction of one portion of the leg gathers 32 on the top-sheet continuous body 121, resulting in inhibition of a product quality failure.

Moreover, the blade section is disposed inside, relative to the crossing direction CD, the outer end region OT. Thereby, the leg gathers 32 located at the outer end region OT are cut by the blade section in a state where the leg gathers 32 are expanded as a result of being held by the outer holding mechanism 650 without the contraction toward the inside of the crossing direction CD. Thus, as compared to the case where the leg gathers 32 are cut in a state where the leg gathers 32 are contracted, it becomes easier to cut the leg gathers 32, resulting in inhibition of a product quality failure.

As a method for preventing the leg gathers 32 from contracting to inside the crossing direction CD without a need for the outer holding mechanism 650 to hold the leg gathers 32, it is possible to conceive a method in which the leg gathers 32 are bonded to the wide top-sheet continuous body 121 onto which the adhesive has been applied.

However, since the top-sheet continuous body 121 has been rendered wide, the top-sheet continuous body 121 to which the adhesive is applied, together with the leg gathers 32, needs to be cut. This increases an amount of materials to be input for the production line for the top-sheet continuous body 121 and increases an amount of waste of the top-sheet continuous body 121 while it is cut. As a result, manufacture cost increases. In addition, at the time of cutting, the adhesive adheres to the blade section, resulting in a decrease in durability of the blade section.

To solve this problem, the outer holding mechanism 650 holds the leg gathers 32 located at the outer end region OT without rendering the top-sheet continuous body 121 wide. This serves to reduce the manufacture cost without increasing the amount of materials for the top-sheet continuous body 121 and increasing the waste of the top-sheet continuous body 121. Moreover, the adhesive has not been applied to the outer end region OT held by the outer holding mechanism 650, and thus, the adhesive does not easily adhere to the blade section. As a result, even the durability of the blade section is improved.

Thus, based on the diaper manufacturing apparatus 500 according to the first embodiment, it is possible to inhibit the product quality failure while serving to reduce the manufacture cost of the product and securing the fit to the wearer (in particular, to the leg girth portions 30).

In the first embodiment, the inner holding mechanism 600 holds the top sheet continuous body 121 in which the leg gathers 32 are disposed in a predetermined waveform by the oscillating mechanism 520. According thereto, it is possible to more surely bond the one portion of the leg gathers 32 to the top-sheet continuous body 121. This eliminates a chance that the leg gathers 32 are bonded to the top-sheet continuous body 121 when the leg gathers 32 are contracted, resulting in the fit being secured to the wearer.

In the first embodiment, the surface 121B of the top-sheet continuous body 121 runs along the outer circumferential surface of the drum main body 510, and on the surface 121A of the top-sheet continuous body 121, the flat belts 660 hold the elastic member toward the drum main body 510. According thereto, between the outer circumferential surface of the drum main body 510 and the flat belts 660, the leg gathers 32 located at the outer end region OT can be surely held. This enables a much ensured prevention of the instantaneous contraction of one portion of the leg gathers 32 disposed to be deviated from the top-sheet continuous body 121.

In the first embodiment, on the top surface of the flat belts 660, the concave sections 662 with which at least one portion of the round belts 670 is fitted via the leg gathers 32 are formed. That is, the flat belts 660 and the round belts 670 work together to sandwich the leg gathers 32 located at the outer end region OT. According thereto, between the flat belts 660 and the round belts 670, the leg gathers 32 deviated from the top-sheet continuous body 121 can be surely held down. This enables a much ensured prevention of the instantaneous contraction of one portion of the leg gathers 32.

In the first embodiment, between the drum main body 510 and the flat belts 660, the round belts 670 thinner than the width of the flat belts 660 are disposed. According thereto, between the flat belts 660 and the round belts 670, the leg gathers 32 located at the outer end region OT can be surely held down. Moreover, since it is possible to convey the top sheet continuous body 121 in a state where the leg gathers 32 are sandwiched between the flat belts 660 and the round belts 670, the cutting mechanism 540 can be disposed at a position away from the drum main body 510. Thus, as compared to the case where the cutting mechanism 540 is disposed on the drum main body 510, the freedom to design the cutting mechanism 540 increases.

In the first embodiment, along the outer circumference of the drum main body 510, the concave sections 512 into which the round belts 670 enter are formed. Moreover, along the outer circumference of the round-belt guiding rolls 692, the concave sections 692A into which the round belts 670 enter are formed. According thereto, the round belts 670 stably circle on the outer circumferential surface of the drum main body 510 and on the outer circumferential surface of the round-belt guiding rolls 692.

In this case, if the depth of the concave sections 512 is deeper than the thickness of the round belts 670, then the round belts 670 enter into the concave sections 512. As a result, it often becomes difficult to sandwich the leg gathers 32 between the flat belts 660 and the round belts 670. Thus, the depth of the concave sections 512 is set to be shallower than the thickness of the round belts 670.

In the first embodiment, as a result of overlapping the rim or one portion of the lower blade 751, the rim or one portion of the upper blade 711 sandwiches and cuts at least the leg gathers 32. According thereto, as compared to the case where the leg gathers 32 are torn off while pressing (press-cutting), the leg gathers 32 can be more surely cut.

In the first embodiment, the flat belts 660 and the round belts 670 are formed by using an elastic member (e.g., a rubber material). According thereto, the flat belts 660 and the round belts 670 come to easily run along the outer circumferential surface of the drum main body 510, and thus, the leg gathers 32 deviated from the top-sheet continuous body 121 can be more surely held down.

In the first embodiment, the outer holding mechanism 650 holds only the leg gathers 32 located at the outer end region OT, and the blade section (the upper blade roll 710 and the lower blade roll 750) cuts only the leg gathers 32 held by the outer holding mechanism 650. According thereto, as compared to the case where the top-sheet continuous body 121 and the leg gathers 32 are cut, the top-sheet continuous body 121 will not be wasted and thus the loss of the top-sheet continuous body 121 can be reduced. Thus, it is possible to inhibit the product quality failure while serving to reduce the manufacture cost of the product.

Moreover, the blade section cuts the leg gathers 32 only, and thus, the top-sheet continuous body 121 to which the adhesive is applied is not cut; the adhesive does not adhere to the blade section; and the durability of the blade section is improved.

In the first embodiment, in one waveform deviated from the top-sheet continuous body 121 (WV in FIG. 6), the outer holding mechanism 650 holds the leg gather 32 at no less than two or more holding points, toward the outer circumferential surface of the drum main body 510. For example, in a case where the outer holding mechanism 650 holds the leg gathers 32 near the width-direction end 121e of the top-sheet continuous body 121 at two holding points, the leg gathers 32 can be disposed on the top-sheet continuous body 121 in an arbitrary predetermined waveform in a portion outside, relative to the crossing direction CD, the holding points. Thus, the freedom to design the leg gathers 32 increases.

Moreover, in the portion outside, relative to the crossing direction CD, the holding points, even if the leg gathers 32 contract toward inside the crossing direction CD, the expansion state of the leg gathers 32 can be surely maintained in the portion inside the crossing direction CD from the holding points. Thus, it is possible to more surely cut the leg gathers 32 and to inhibit the product quality failure.

[Second Embodiment]

Hereinafter, a diaper manufacturing apparatus 500A based on a second embodiment according to the present invention will be explained with reference to diagrams. It is noted that the same components of the diaper manufacturing apparatus 500 according to the first embodiment are assigned the same numerals, and different portions will be primarily explained.

Figure 11:
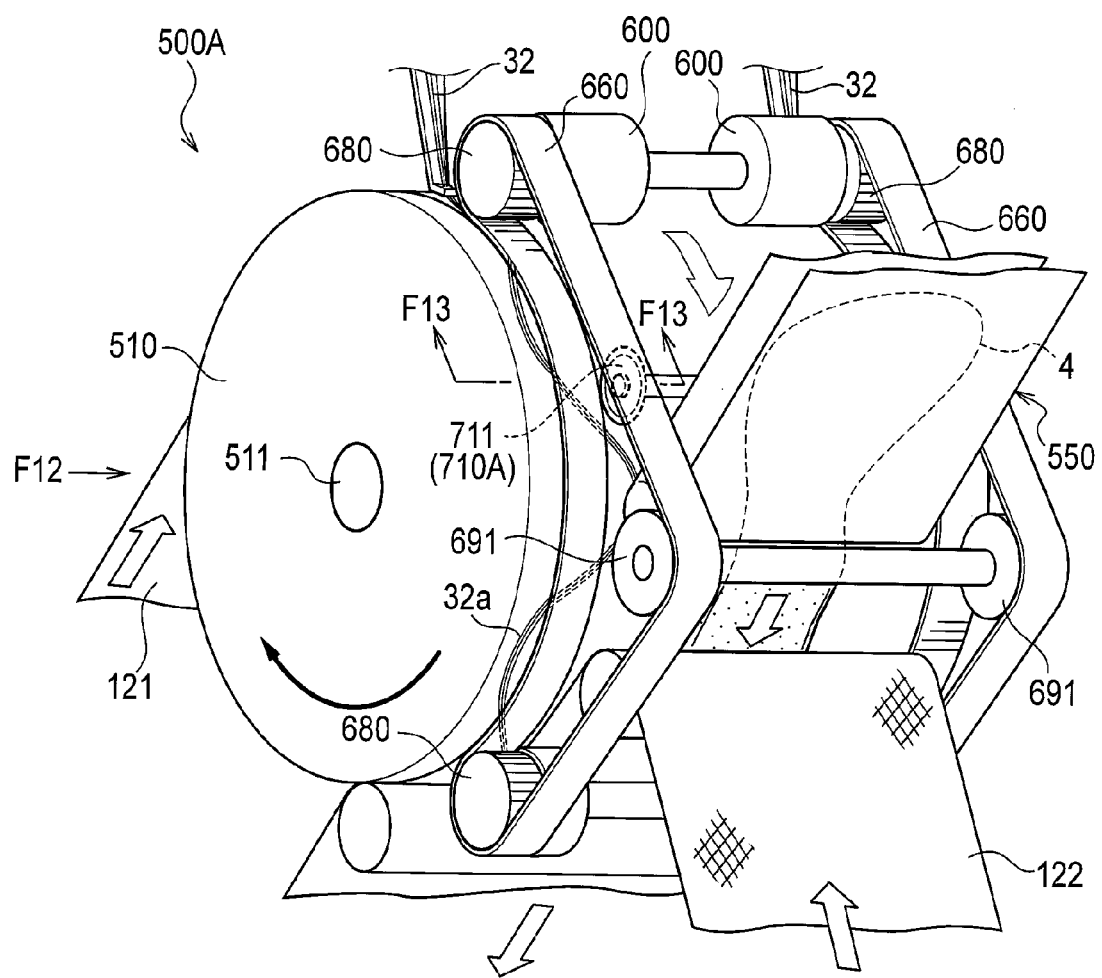
[FIG. 11]
Figure 12:
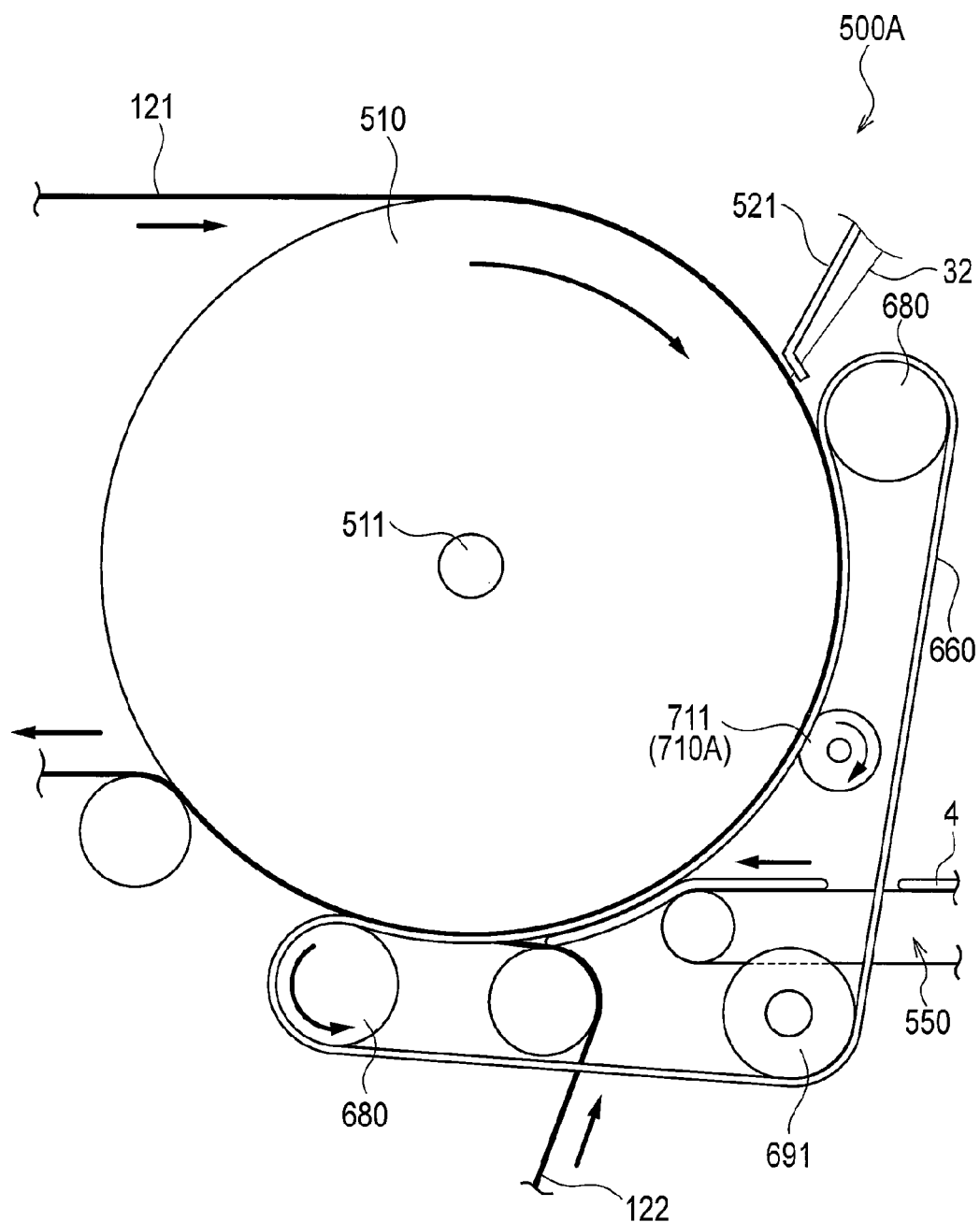
[FIG. 12]

FIG. 11 is a perspective view showing the diaper manufacturing apparatus 500A according to the second embodiment. FIG. 12 is a side view showing the diaper manufacturing apparatus 500A, as seen from an F12 direction of FIG. 11. FIGS. 13 (A) and 13 (B) are a cross-sectional view showing one portion of the diaper manufacturing apparatus 500A along a line F13-F13 in FIG. 11.

In this case, in the diaper manufacturing apparatus 500 according to the first embodiment, the cutting mechanism 540 is disposed below the drum main body 510 and downstream of the drum main body 510. Moreover, the outer holding mechanism 650 includes the round belts 670.

On the other hand, in the diaper manufacturing apparatus 500A according to the second embodiment, the cutting mechanism 540A is disposed on the outer circumferential surface of the drum main body 510. Further, the outer holding mechanism 650 does not include the round belts 670.

Specifically, as shown in FIG. 11 and FIG. 12, the cutting mechanism 540A cuts the leg gathers 32 when the leg gathers 32 are held by the flat belts 660 toward the outer circumferential surface of the drum main body 510. The cutting mechanism 540A is configured of an upper blade roll 710A and a lower blade 751A (second blade, see FIGS. 13 (A) and 13 (B)).

In the upper blade roll 710A, an upper blade 711A (first blade) capable of rotating along the machine direction MD is arranged. The upper blade 711A comes into contact with the leg gathers 32 on a surface 121A of the top-sheet continuous body 121, and cuts the leg gathers 32. The upper blade roll 710A is disposed downstream, relative to the machine direction MD, of the oscillating mechanism 520, and disposed upstream, relative to the machine direction MD, of the absorber disposing mechanism 550 and the back-sheet pressing mechanism 560.

The lower blade 751A is arranged along the outer circumference of the drum main body 510 and is capable of rotating along the machine direction MD. As shown in FIG. 13 (A), on the outer circumferential surface of the drum main body 510, the lower blade 751A is arranged flush with the outer circumferential surface of the drum main body 510. The lower blade 751A comes into contact with the leg gathers 32 on a surface 121B of the top-sheet continuous body 121, and cuts the leg gathers 32.

It is not necessarily needed that the lower blade 751A is arranged flush with the outer circumferential surface of the drum main body 510. The lower blade 751A may be recessed from the outer circumferential surface of the drum main body 510 toward the axial core 511 and may be a concave section 751B into which the upper blade 711A enters on the outer circumferential surface of the drum main body 510, as shown in FIG. 13 (B).

In the second embodiment thus described, the upper blade roll 710A is disposed downstream, relative to the machine direction MD, of the oscillating mechanism 520, and disposed upstream, relative to the machine direction MD, of the absorber disposing mechanism 550 and the back-sheet pressing mechanism 560. Moreover, the lower blade 751A is arranged on the outer circumferential surface of the drum main body 510. According thereto, unlike the case where the cutting mechanism 540 is disposed from the drum main body 510, it is possible to achieve a compact apparatus, secure the fit to the wearer, and inhibit a product quality failure.

[Other Embodiments]

As described above, the content of the present invention has been disclosed through the embodiments of the present invention; it should not be understood that the description and the diagrams, one portion of the disclosure, restrict the present invention. From this disclosure, a variety of alternate embodiments, examples, and applicable techniques will be apparent to one skilled in the art.

For example, the embodiments of the present invention can be modified as follows: The diaper 1 has been explained as a disposable diaper; however, this is not always the case. The diaper 1 may be a wearing article, such as disposable pants, in which the absorber 4 is not arranged. Moreover, it is needless to say that the diaper 1 is not limited to the configuration explained in the first embodiment and can be appropriately set according to purpose.

The diaper 1 has been formed by combining the pair of waistline sections 10 and the inner leg section 20; however, this is not always the case. The whole of the pair of waistline sections 10 and the inner leg section 20 may be formed as one body.

Moreover, the diaper manufacturing apparatus 500 includes: the drum main body 510; the oscillating mechanism 520; the holding mechanism 530; the cutting mechanism 540; the absorber disposing mechanism 550; the back-sheet pressing mechanism 560; the sheet conveyance mechanism 570; the rubber collection mechanism 580; and the sheet guiding roll 590. However, this is not always the case. The diaper manufacturing apparatus 500 may suffice to include at least the oscillating mechanism 520; the holding mechanism 530; and the cutting mechanism 540.

Further, it is needless to say that the configurations of the drum main body 510, the oscillating mechanism 520, the holding mechanism 530, and the cutting mechanism 540 are not limited to those explained in the first embodiment, but can be appropriately set according to purpose. For example, instead of the drum main body 510, a belt conveyer mechanism may be acceptable. Moreover, the inner holding mechanism 600 may not necessarily be configured of a pair of roll mechanisms, and may be configured of one roll mechanism.

The cross section along the shorter direction of the endless belt as the flat belts 660 is not necessarily rectangular, and it may be polygonal, circular (elliptical), etc. The shape of the cross section along the shorter direction of the intermediate endless belt as the round belts 670 is not necessarily circular, and it may be elliptical, polygonal (rectangular), etc.

For example, in the case where the intermediate endless belt is rectangular, it is preferable that the convex section mating with the concave sections 662 formed on the surface of the intermediate endless belt, or the convex section into which the concave section 512 formed on the outer circumferential surface of the drum main body 510 is entered is formed. According thereto, between the flat belts 660 and the round belts 670, the leg gathers 32 located at the outer end region OT can be surely held down.

It is noted that the convex section may also be arranged continuously along the rotation direction of the intermediate endless belt and the drum main body 510, and may also be arranged intermittently along the rotation direction. In this case, the concave section 662 and the concave sections 512 may also be arranged intermittently along the rotation direction.

Moreover, in the above embodiments, the outer holding mechanism 650 holds only the leg gathers 32 disposed in a predetermined waveform toward the outer circumferential surface of the drum main body 510; however, this is not always the case. The outer holding mechanism 650 may also hold the top sheet 2 and the leg gathers 32, and may suffice to hold at least the leg gathers 32. Similarly, the blade section does not necessarily need to cut the leg gathers 32 only; it may cut the top sheet 2, the back sheet 3, and the leg gathers 32. In this case, the outer end region OT indicates a vicinity of the width-direction end 121e of the top-sheet continuous body 121.

Moreover, in the above embodiments, when the cutting mechanism 540 cuts the leg gathers 32, the leg gathers 32 are held in the outer end region OT by the outer holding mechanism 650; however, this is not always the case. The inner region IT may also be held by the inner holding mechanism 600 and the lower blade roll 750.

In the above embodiments, the leg gathers 32 are disposed in the top-sheet continuous body 121; however, this is not always the case. The leg gathers 32 may be disposed in the back-sheet continuous body 122, for example.

Further, in the above embodiments, the oscillating mechanism 520 disposes the leg gathers 32 corresponding to the leg girth portions 30 of the diaper 1 in the top-sheet continuous body 121; however, this is not always the case. The oscillating mechanism 520 may dispose the waist gather 31 corresponding to the leg girth portions 30 of the diaper 1 in a sheet-like continuous body (e.g., the top-sheet continuous body 121), for example. That is, it is needless to say that the diaper manufacturing apparatus 500 may suffice to be used for manufacturing the disposable wearing article.

Thus, needless to say, the present invention includes a variety of embodiments not described here. Therefore, the technical scope of the present invention is only defined by the invention specific matters according to the claims reasonably derived from the above description.

The entire contents of Japanese Patent Application Laid-open No. 2009-233837 (filed on Oct. 7, 2009) are incorporated in the present specification by reference.

[Industrial Applicability]

According to the characteristics of the present invention, in the case where by using the oscillating mechanism, an elastic member is disposed in a waveform having a predetermined amplitude on a sheet-like continuous body such as a conveyed web, it is possible to provide an apparatus for manufacturing a disposable wearing article, capable of securing the fit to a wearer and inhibiting a product quality failure.

The invention claimed is:

1. An apparatus for manufacturing a disposable wearing article, the apparatus comprising:
   a drum main body configured to convey a sheet-shaped continuous body along a conveyance direction,
   an oscillating mechanism configured to feed, while oscillating, an elastic member along a crossing direction crossing the conveyance direction,
      the oscillating mechanism further configured to dispose the elastic member in a predetermined waveform and to dispose a portion of the elastic member in an expanded state onto the continuous body to which an adhesive is applied;
   an outer holding mechanism configured to at least hold the elastic member in the predetermined waveform; and
   a cutting mechanism having a blade section configured to at least cut the elastic member held by the outer holding mechanism, wherein
   the outer holding mechanism is configured to hold an outer end region of an area defined by the predetermined waveform of the elastic member, wherein the outer end region includes an outer end of the elastic member in the crossing direction and is not applied with the adhesive,
   the outer holding mechanism comprises an endless belt rotatable along the conveyance direction of the continuous body,
   the endless belt of the outer holding mechanism includes an arc portion forming an arc shape along an outer circumferential surface of the drum main body,
   the endless belt of the outer holding mechanism is configured to hold the elastic member on a surface of the continuous body on which the elastic member is disposed, toward the drum main body, and
   the blade section is disposed inside, relative to the crossing direction, the outer end region held by the outer holding mechanism.

2. The apparatus according to claim 1, further comprising an inner holding mechanism configured to hold an inner region of the area defined by the predetermined waveform of the elastic member, wherein the inner region is located inside, relative to the crossing direction, the outer end region and is applied with the adhesive.

3. The apparatus according to claim 1, wherein
   the outer holding mechanism further comprises an intermediate endless belt disposed between the drum main body and the endless belt, and
   the endless belt has, on a surface thereof, a concave section facing the intermediate endless belt, the concave section fitted with at least one portion of the intermediate endless belt.

4. The apparatus according to claim 3, wherein
   a shape of a cross section along the crossing direction of the endless belt is a polygon, a length of a side of the polygon along the crossing direction is longer than any other side of the polygon,
   a shape of a cross section along the crossing direction of the intermediate endless belt is circular or elliptical,
   a thickness of the intermediate endless belt is less than a width of the endless belt, and
   a depth of the concave section is less than a height of the intermediate endless belt along a depth direction of the concave section.

5. The apparatus according to claim 3, wherein
   shapes of respective cross sections of the endless belt and the intermediate endless belt along the crossing direction are polygons,
   for each of the polygons, a length of a side of the polygon along the crossing direction is longer than any other side of the polygon, and
   the intermediate endless belt, on a surface thereof, has a convex section mating with the concave section of the endless belt.

6. The apparatus according to claim 1, wherein
   the outer holding mechanism further comprises an intermediate endless belt disposed between the drum main body and the endless belt,
   the drum main body has, on an outer circumferential surface thereof, a drum-side concave section into which at least one portion of the intermediate endless belt enters, and
   a depth of the drum-side concave section is less than a height of the intermediate endless belt along a depth direction of the drum-side concave section.

7. The apparatus according to claim 1, wherein
   the blade section comprises:
      a first blade configured to come into contact with the elastic member on said surface of the continuous body and to cut at least the elastic member; and
      a second blade configured to come into contact with the elastic member on the other surface of the continuous body and to cut at least the elastic member,
   the first blade is rotatable along the conveyance direction of the continuous body, and
   the second blade is rotatable along the conveyance direction of the continuous body in a manner to contact with at least one portion of the first blade
   to sandwich and cut at least the elastic member.

8. The apparatus according to claim 3, wherein
   at least either one of the endless belt or the intermediate endless belt is formed of an elastic material.

9. The apparatus according to claim 1, wherein
   the outer end region is a region in which the elastic member only is disposed and the outer end region is further outside an outer end of the continuous body in the crossing direction, and
   the outer holding mechanism is configured to hold only the elastic member located at the outer end region.

10. The apparatus according to claim 9, wherein
    the blade section is configured to cut only the elastic member held by the outer holding mechanism.

* * * * *